United States Patent
Grim et al.

(10) Patent No.: US 7,288,076 B2
(45) Date of Patent: Oct. 30, 2007

(54) SELF-EQUALIZING RESILIENT ORTHOPAEDIC SUPPORT

(75) Inventors: Tracy Grim, Tulsa, OK (US); William K. Arnold, Woodland Hills, CA (US); Joseph M. Iglesias, Thousand Oaks, CA (US)

(73) Assignee: Ossur hf, Reykjavik (IS)

(*) Notice: Subject to any disclaimer, the term of this patent is extended or adjusted under 35 U.S.C. 154(b) by 264 days.

(21) Appl. No.: 10/371,018

(22) Filed: Feb. 21, 2003

(65) Prior Publication Data
US 2003/0171703 A1  Sep. 11, 2003

Related U.S. Application Data

(63) Continuation-in-part of application No. 09/857,396, filed as application No. PCT/US97/15265 on Aug. 29, 1997, now Pat. No. 7,018,351, which is a continuation-in-part of application No. 08/705,218, filed on Aug. 29, 1996, now abandoned.

(51) Int. Cl.
*A61F 5/00* (2006.01)
(52) U.S. Cl. ............................................ 602/5; 602/27
(58) Field of Classification Search ................ 602/4–5, 602/16, 20–23, 26–27, 13; 128/882
See application file for complete search history.

(56) References Cited

U.S. PATENT DOCUMENTS

| | | |
|---|---|---|
| 5,328,445 A | 7/1994 | Spahn et al. |
| 5,435,009 A | 7/1995 | Schild et al. |
| 5,445,602 A * | 8/1995 | Grim et al. .................... 602/27 |
| 5,496,262 A * | 3/1996 | Johnson et al. .............. 601/152 |
| 5,626,557 A | 5/1997 | Mann |
| 5,795,312 A | 8/1998 | Dye |
| 5,813,144 A | 9/1998 | Prengler |
| 5,833,639 A | 11/1998 | Nunes et al. |
| 5,954,676 A | 9/1999 | Kramer, III |
| 6,045,519 A | 4/2000 | Smith, Sr. |
| 6,447,467 B1 | 9/2002 | Barak |
| 6,689,081 B2 * | 2/2004 | Bowman ..................... 602/27 |

* cited by examiner

*Primary Examiner*—Michael A. Brown
(74) *Attorney, Agent, or Firm*—Bacon & Thomas, PLLC

(57) ABSTRACT

An ankle brace has first and second semi-rigid shell members for extending over the ankle and the lower leg on the inner and outer sides of the ankle. A sealed bladder pad is mounted to each of the shell members on the side of the shell member facing the ankle. Each bladder pad includes three small-interconnected bladders wherein a first larger bladder is mounted at the lower end of the shell, and two side-by-side upper bladders are mounted on an upper portion of the associated shell member. The three bladders having restricted openings permitting limited flow of air between the bladders. When a patient wearing the ankle brace walks, the lower bladder is compressed, and air is directed through the restricted openings to the upper bladders, thereby intermittently varying the pressure on the ankle and lower leg, and promoting circulation.

17 Claims, 13 Drawing Sheets

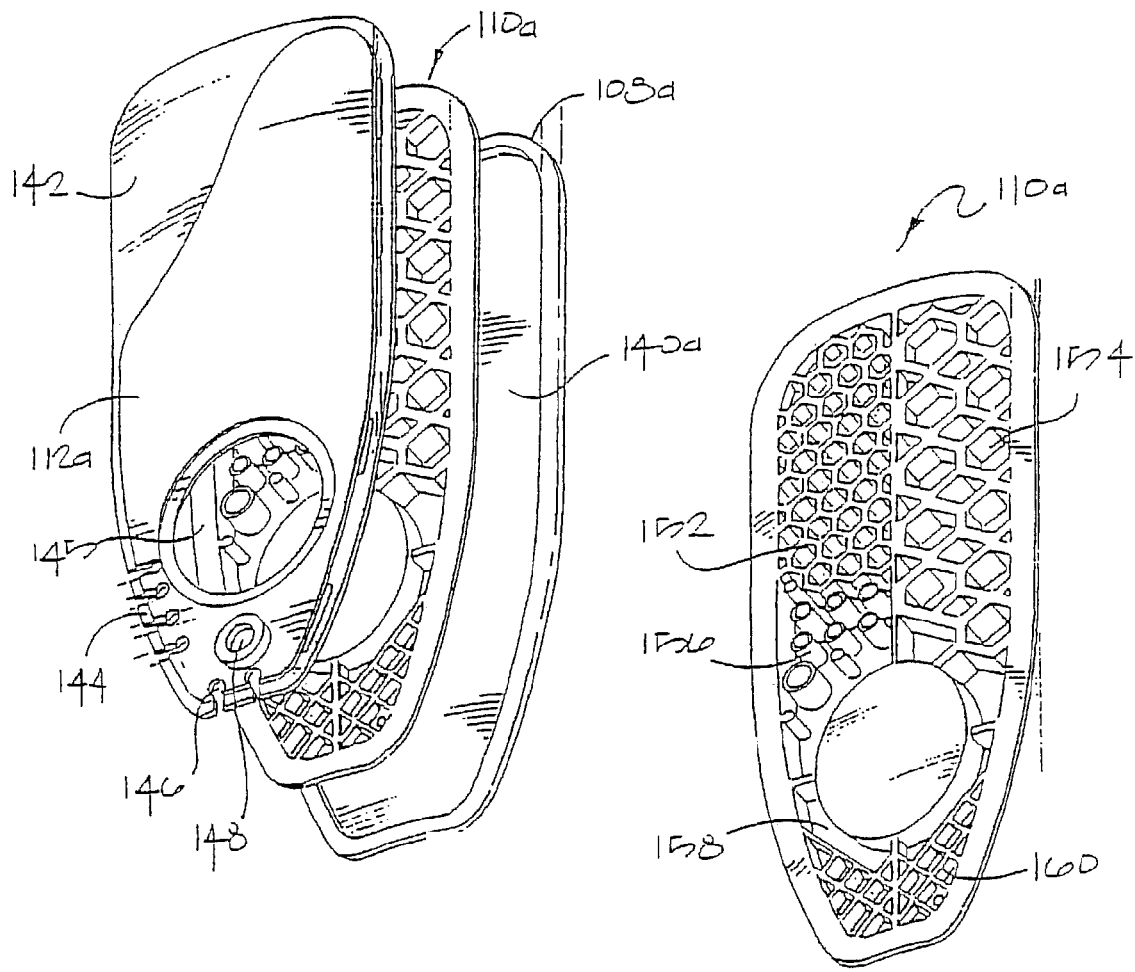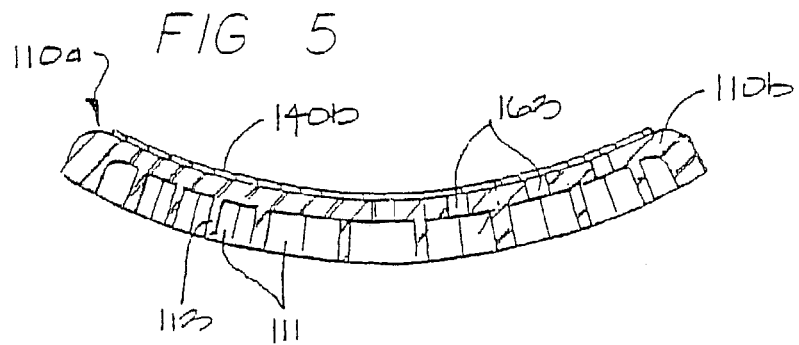

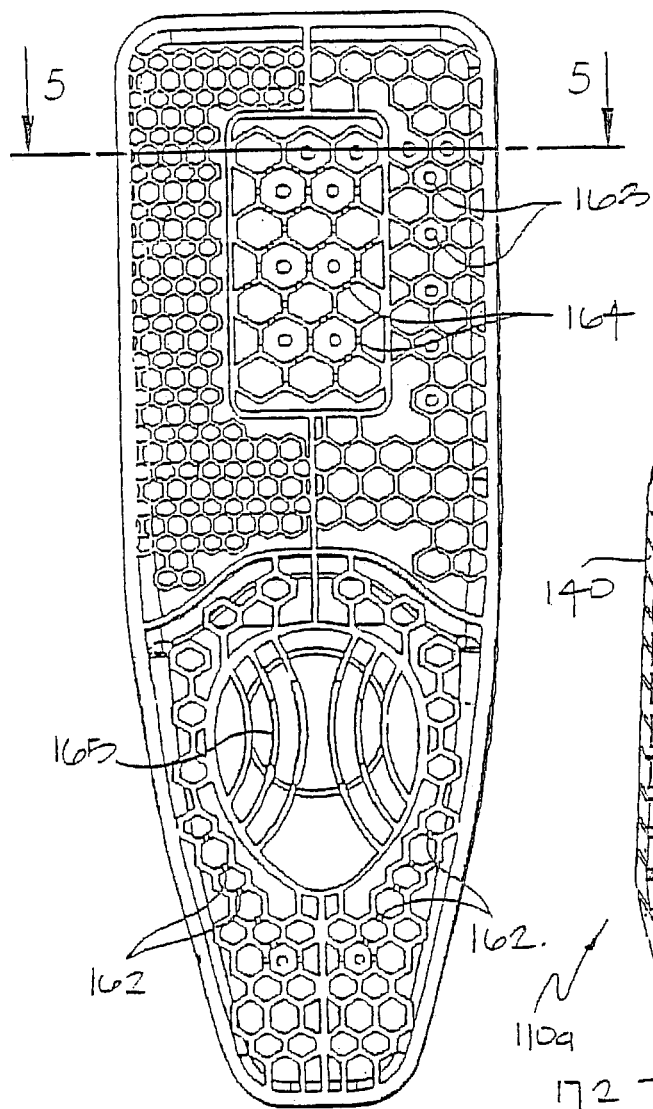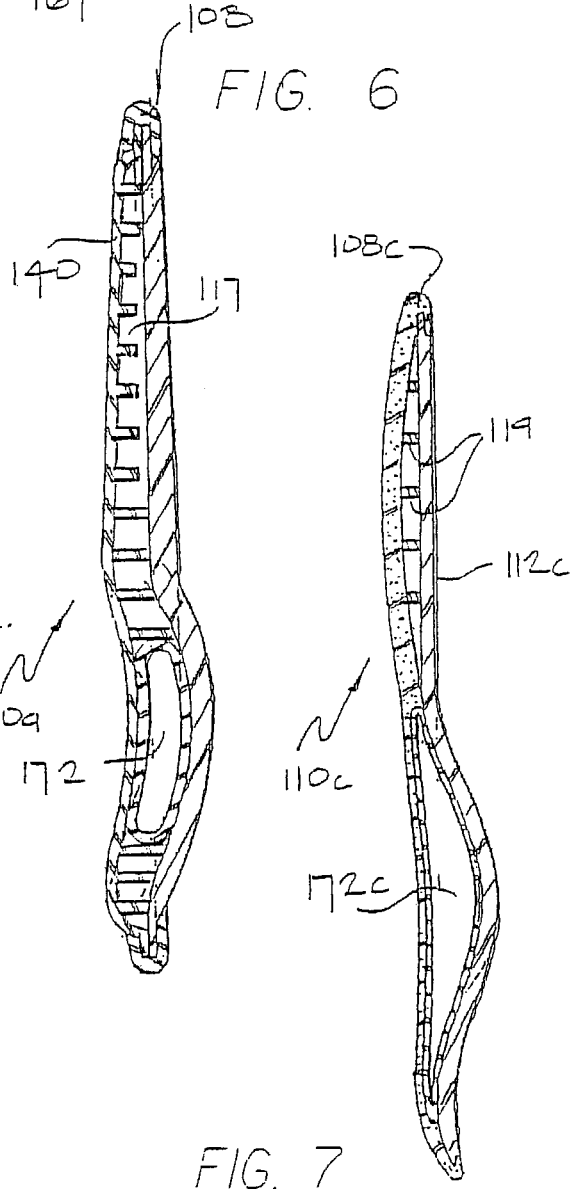

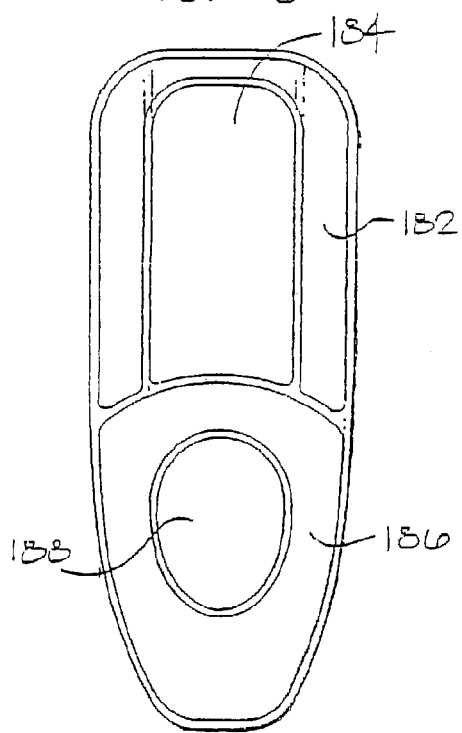
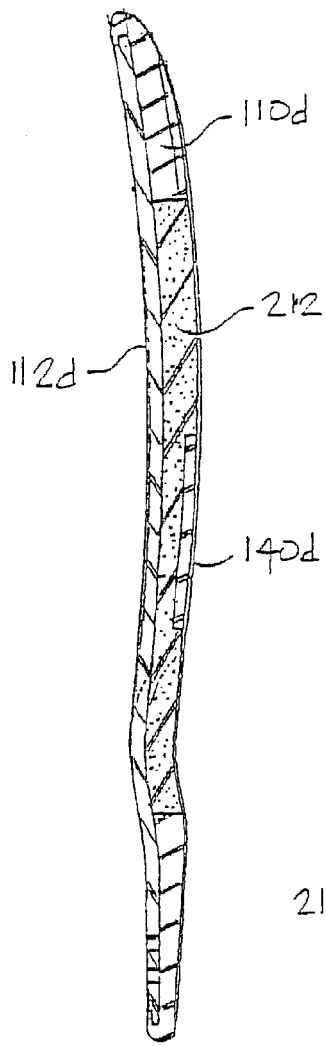
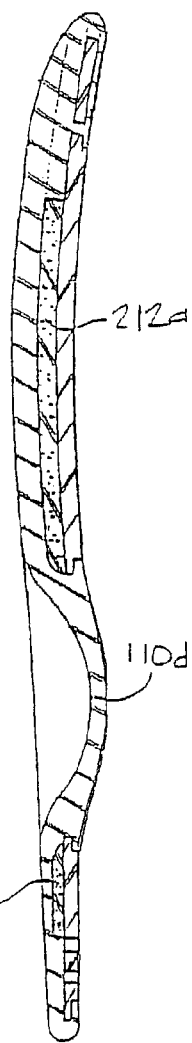
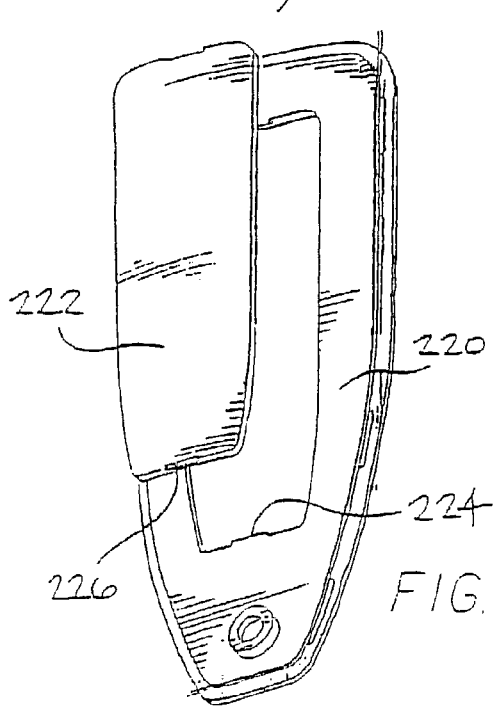

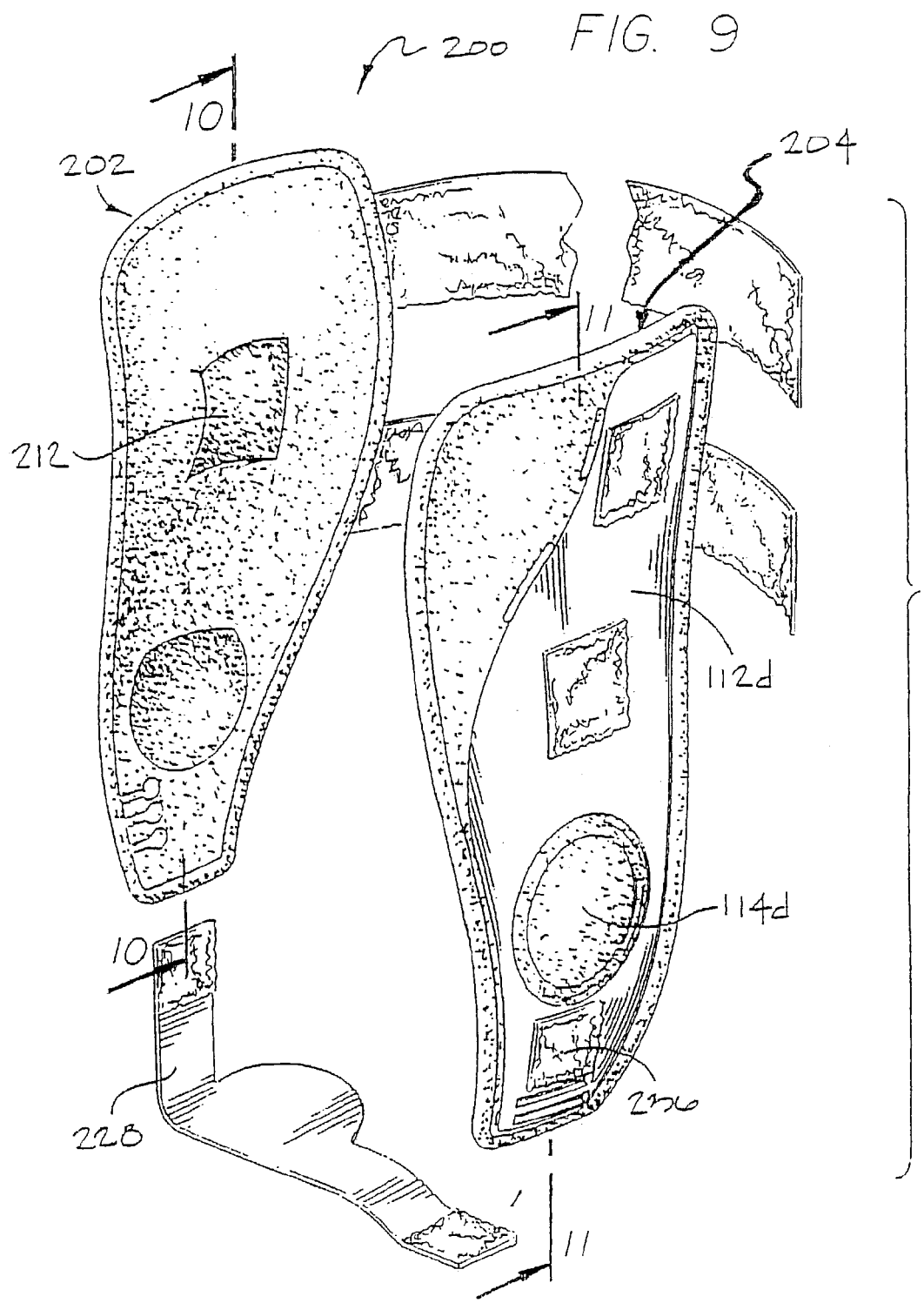

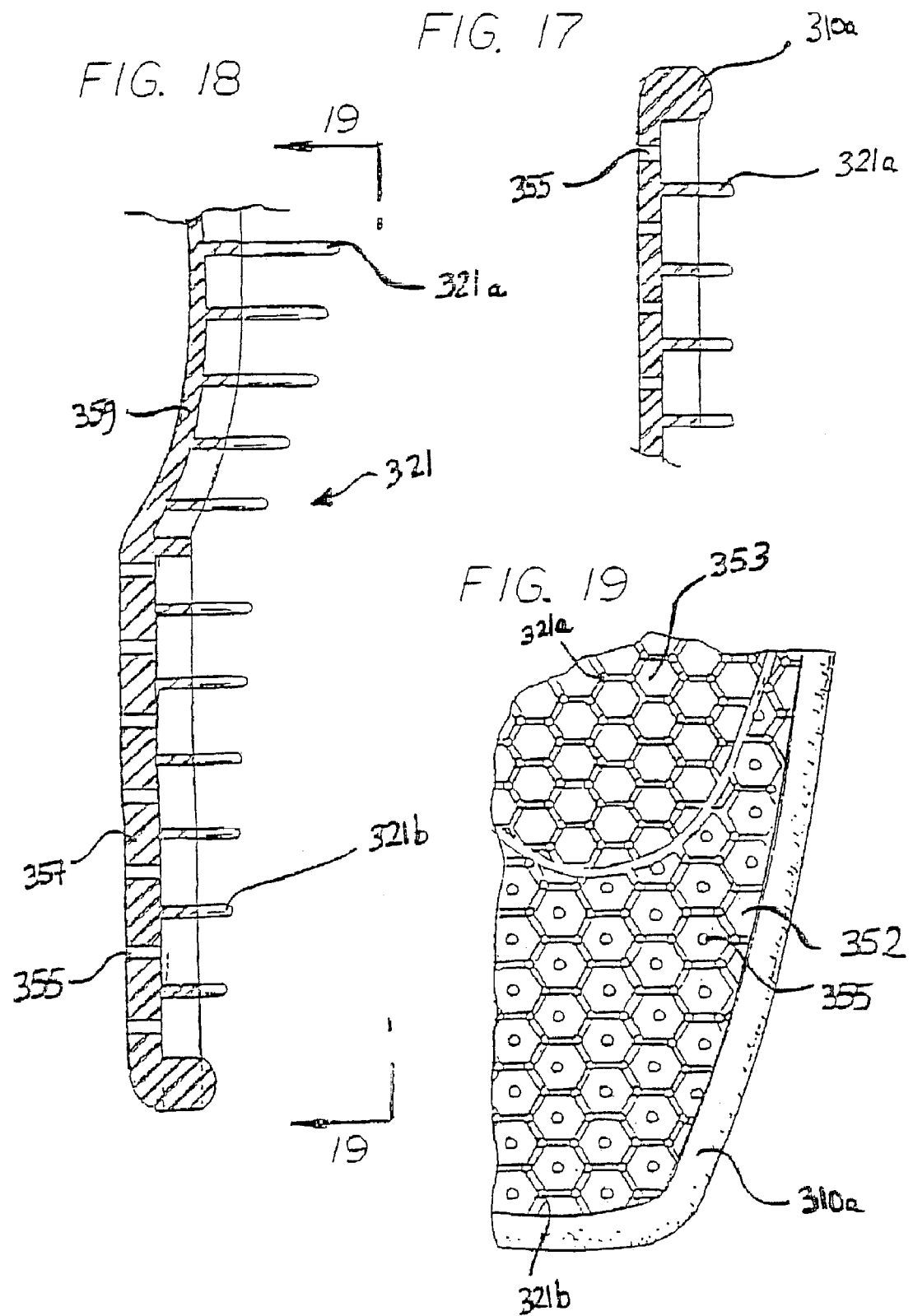

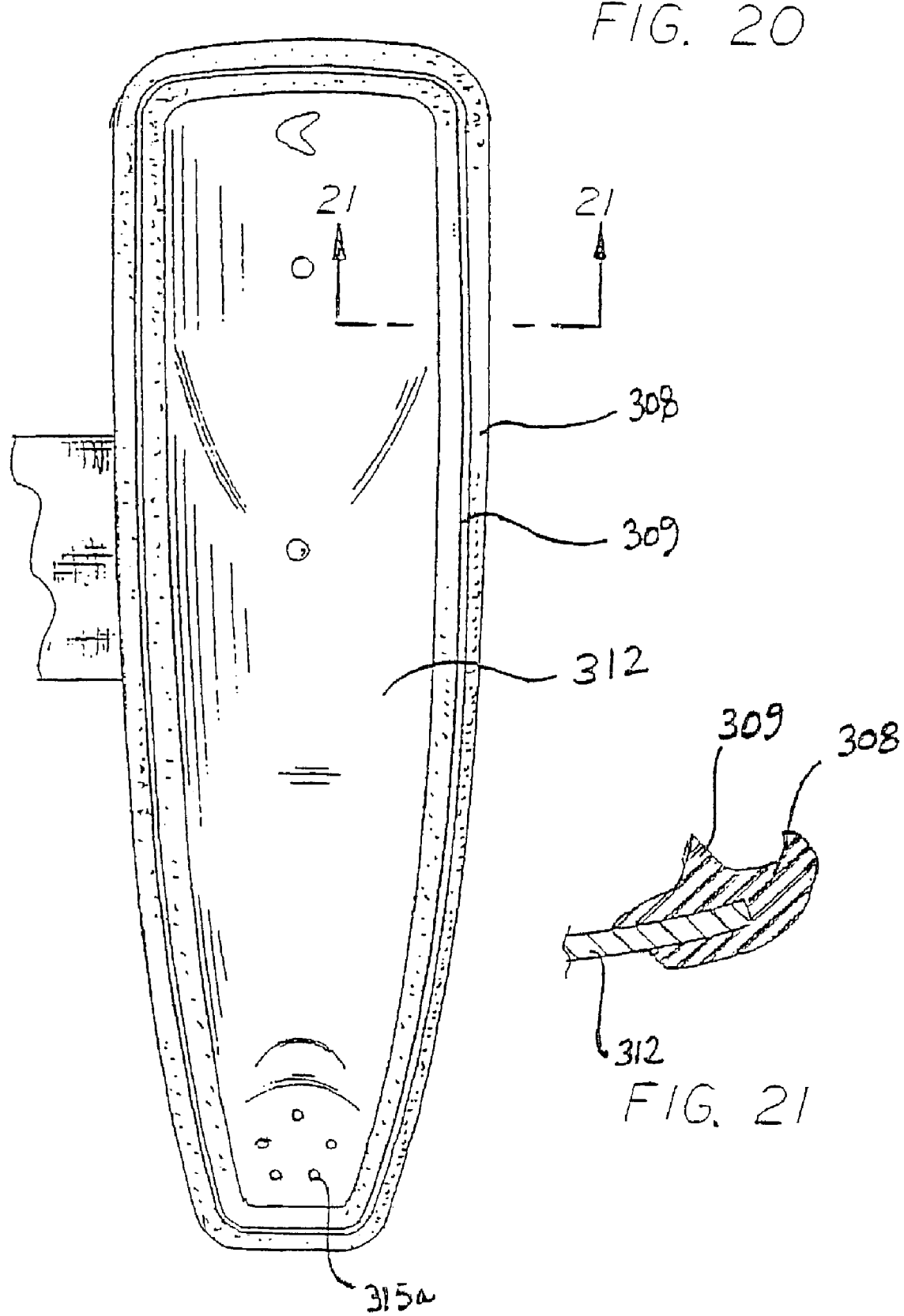

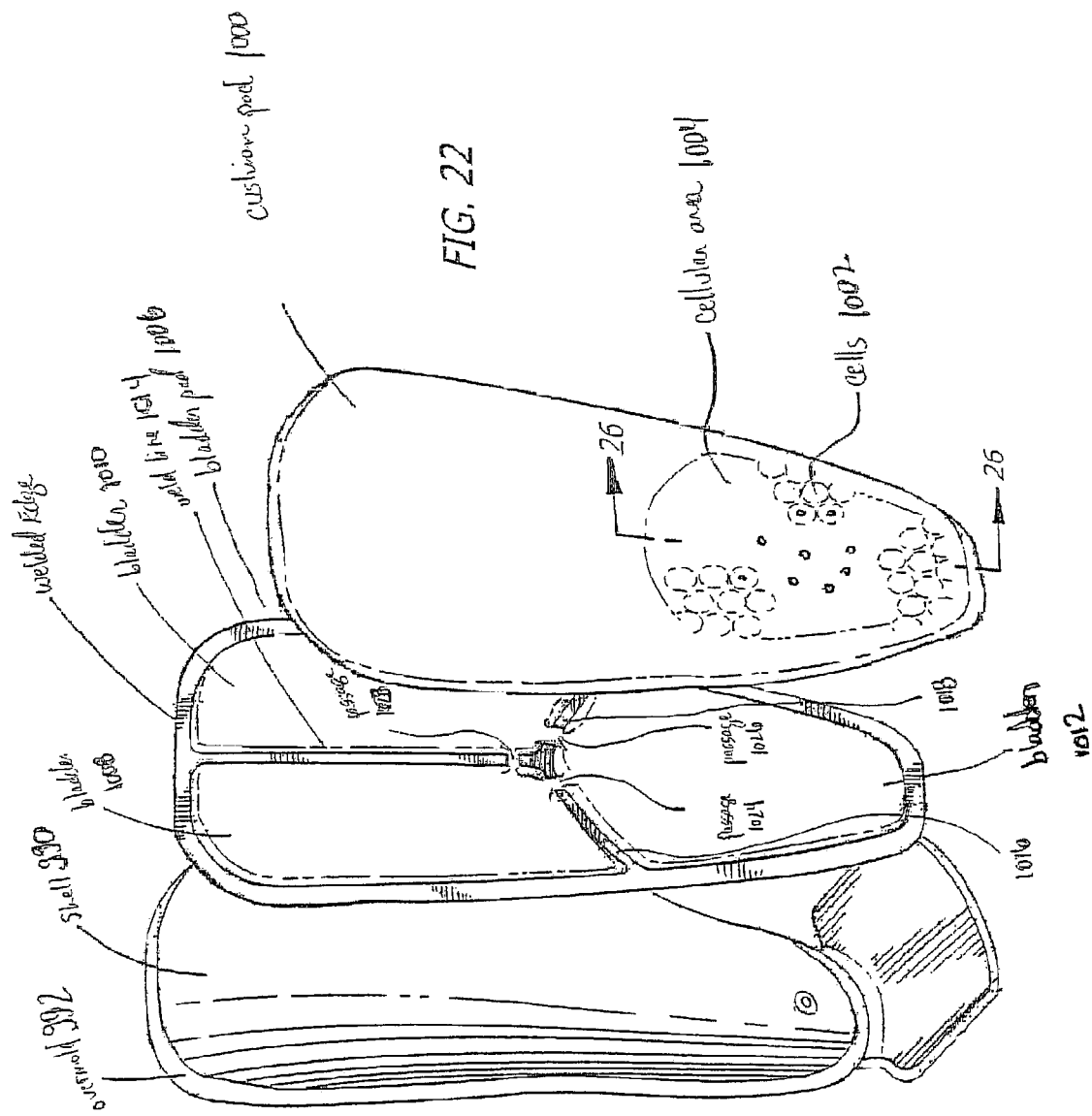

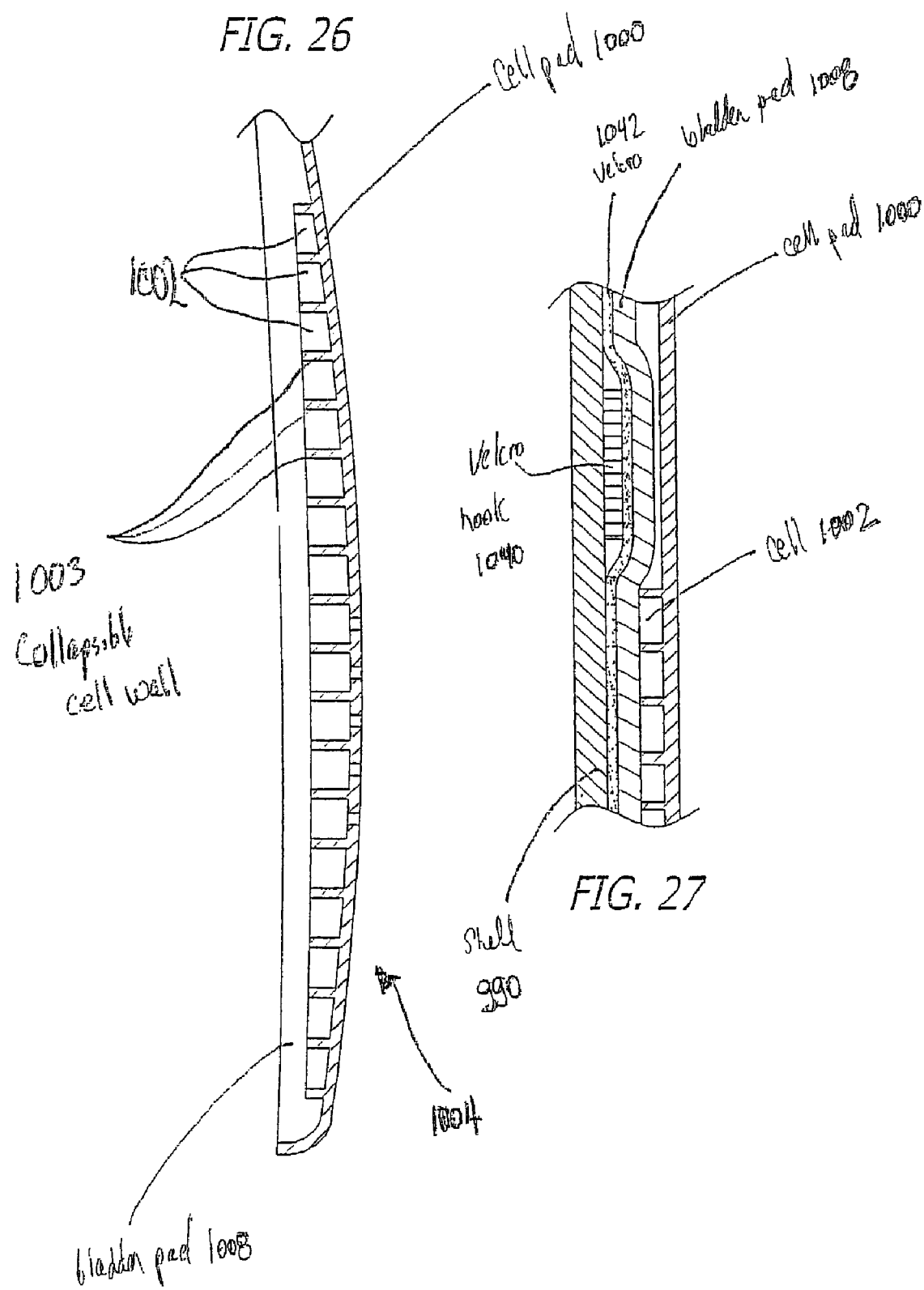

SELF-EQUALIZING RESILIENT ORTHOPAEDIC SUPPORT

RELATED APPLICATION

This application is a continuation-in-part of U.S. application Ser. No. 09/857,396, filed May 31, 2001, now U.S. Pat. No. 7,018,351, which is a national phase entry of international application no. PCT/US97/15265, filed internationally on Aug. 29, 1997, which is a continuation-in-part of U.S. application Ser. No. 08/705,218, filed Aug. 29, 1996, now abandoned, all of whose contents are hereby incorporated by reference.

FIELD OF THE INVENTION

The present invention generally relates to an improved orthopedic device, and specifically to a orthopedic support for body limbs or joints with emphasis on the construction of the support for comfort fit.

DESCRIPTION OF RELATED ART

U.S. Pat. No. 5,125,400 discloses an ankle brace having sidewall members with inflatable air cells. One air cell is the same length as its corresponding sidewall member, while a second air cell is shorter. The air cells are arranged in an overlapping manner.

U.S. Pat. No. 5,496,262 discloses a brace having a pressure source that provides intermittent pressure pulses to fluid that fills inflatable chambers. The brace has fluid exhaust means that continuously exhausts the fluid from the inflatable chambers to atmosphere.

SUMMARY OF THE INVENTION

One specific, non limiting embodiment of the invention is an ankle brace having first and second semi-rigid shell members for extending over the ankle and the lower leg on the inner and outer sides of the ankle, and a sealed bladder pad mounted to each of the shell members on the side of the shell member facing the ankle. It should be noted that a semi-rigid shell member is desired; however, in some embodiments that shell member may be more or less rigid. Each bladder pad includes interconnected bladders on the pad. In one particular embodiment, there are three such bladders formed on the pad. In this embodiment, a first larger bladder is mounted at the lower end of the shell, and two side-by-side upper bladders are mounted on an upper portion of the associated shell member. The three bladders have restricted openings permitting limited flow of air between at least some of the bladders. When a patient wearing the ankle brace walks, the lower bladder is compressed, and air is directed through the restricted openings to the upper bladders, thereby intermittently varying the pressure on the ankle and lower leg, and promoting circulation.

Another specific embodiment is an ankle brace having first and second semi-rigid shell members for extending over the ankle and the lower leg on the inner and outer sides of the ankle. Onto each of the shell members on the side of the shell member facing the ankle, there is mounted a respective bladder pad. Each bladder pad includes three small interconnected bladders wherein a first larger bladder is mounted at the lower end of the shell, and two side-by-side upper bladders are mounted on an upper portion of the associated shell member; the three bladders having restricted openings permitting limited flow of air between the bladders; and resilient cushioning material mounted to each the shell and the bladders on the side of the shell facing the ankle; whereby when a patient wearing the ankle walks, the lower bladder is compressed, and air is directed through the restricted openings to the upper bladders, thereby intermittently varying the pressure on the ankle and lower leg, and promoting circulation.

Optional aspects of the invention include one or more special features. The cushioning material may be a thin layer of resilient material substantially coextensive with each the bladder. The cushioning material may be a plastic sheet with geometric shapes thereon extending outward from the plastic sheet, toward the shell. The resilient material may be loop type padding material, and the hook type material may be bonded to the shells for hook and loop type mounting of the resilient material to the shells.

Considering another embodiment, an ankle brace has first and second semi-rigid shell members for extending over the ankle and the lower leg on the inner and outer sides of the ankle. A sealed bladder pad is mounted to each of the shell members on the side of the shell member facing the ankle. Each bladder pad includes a plurality of interconnected bladders. At least two of the bladders have restricted openings permitting limited flow of air between the at least two bladders. A resilient pad has resilient geometric shapes thereon extending toward the shell, and is bonded to said shell covering said bladder around the periphery of the shell.

Considering other possible aspects, the resilient geometric shapes are in the lower half of the resilient pad. The geometric shapes may be ellipses. An overmold may substantially surround the shell and the pad may be bonded to the overmold, substantially sealing together the orthopedic support. The ankle brace may further comprise means for securing the ankle support around the lower leg. The pad may further comprise a plurality of integrally molded fingers and/or other shapes extending from the pad to the outer shell. These shapes may be integrally molded with the pad, or as separate molded structures. Some of the fingers may have a different length than others of the fingers. The pad may be formed of a thermoplastic elastomer (TPE).

It should be noted that specific embodiments of the invention may include the bladder pad, but not the cell pad. A layer of padding material other than a cell pad may be interposed in between the bladder pad and the skin of the user. Or, in some embodiments, the bladder pad may be placed directly on the skin of the user.

Other aspects, features, and advantages of the present invention will be apparent to those persons having ordinary skill in the art to which the present invention relates from the foregoing description and the accompanying drawings.

BRIEF DESCRIPTION OF THE DRAWINGS

FIG. 2 is an exploded view of the ankle support shown in FIG. 1, and illustrating the construction of the ankle support;

FIG. 3 is a perspective detailed view of the internal cell structure of the thermoplastic elastomer (TPE) pad illustrated by FIG. 2;

FIG. 4 illustrates various internal geometric shaped cells and channels of the TPE pad;

FIG. 5 is a partial transverse cross-sectional view of the pad shown in FIG. 4 taken along lines 5-5 of FIG. 4.

FIG. 6 is a cross-sectional side view illustrating the structure of one alternative embodiment of the ankle support shown in FIG. 1, taken along lines 6-6 of FIG. 1;

FIG. 7 is an cross-sectional side view of an alternative embodiment of an ankle support;

FIG. 8 illustrates the areas of the ankle support which may require differing levels of cushioning and support;

FIG. 9 is a diagrammatic, perspective view of an alternative embodiment of the ankle support of the present invention employing foam material for cushioning;

FIG. 10 is a cross-sectional side view illustrating the ankle support pad structure, taken along lines 10-10 of FIG. 9;

FIG. 11 is a cross-sectional side view illustrating the ankle support pad structure of an alternative embodiment;

FIG. 12 illustrates an alternative embodiment of the shell with a removable core for varying the rigidity of the shell;

FIG. 17 is a cross-sectional view taken across line 17-17 of FIG. 16;

FIG. 18 is a cross-sectional view taken across line 18-18 of FIG. 16;

FIG. 19 is a detail perspective view of an interior portion of the pad of FIG. 16;

FIG. 20 is a perspective view of a shell to which the pad of FIG. 16 is to be bonded;

FIG. 21 is a cross-sectional view taken along line 21-21 of FIG. 20 illustrating the overmold that is molded about the edges of the shell itself;

FIG. 22 is a view of an alternative ankle brace embodiment;

FIG. 26 is a cross-sectional view showing a tapered cell pad; and

FIG. 27 is a cross-sectional view of a further alternative embodiment using velcro to attach the bladder pad to the shell.

DETAILED DESCRIPTION OF THE PREFERRED EMBODIMENT(S)

Figure 1:
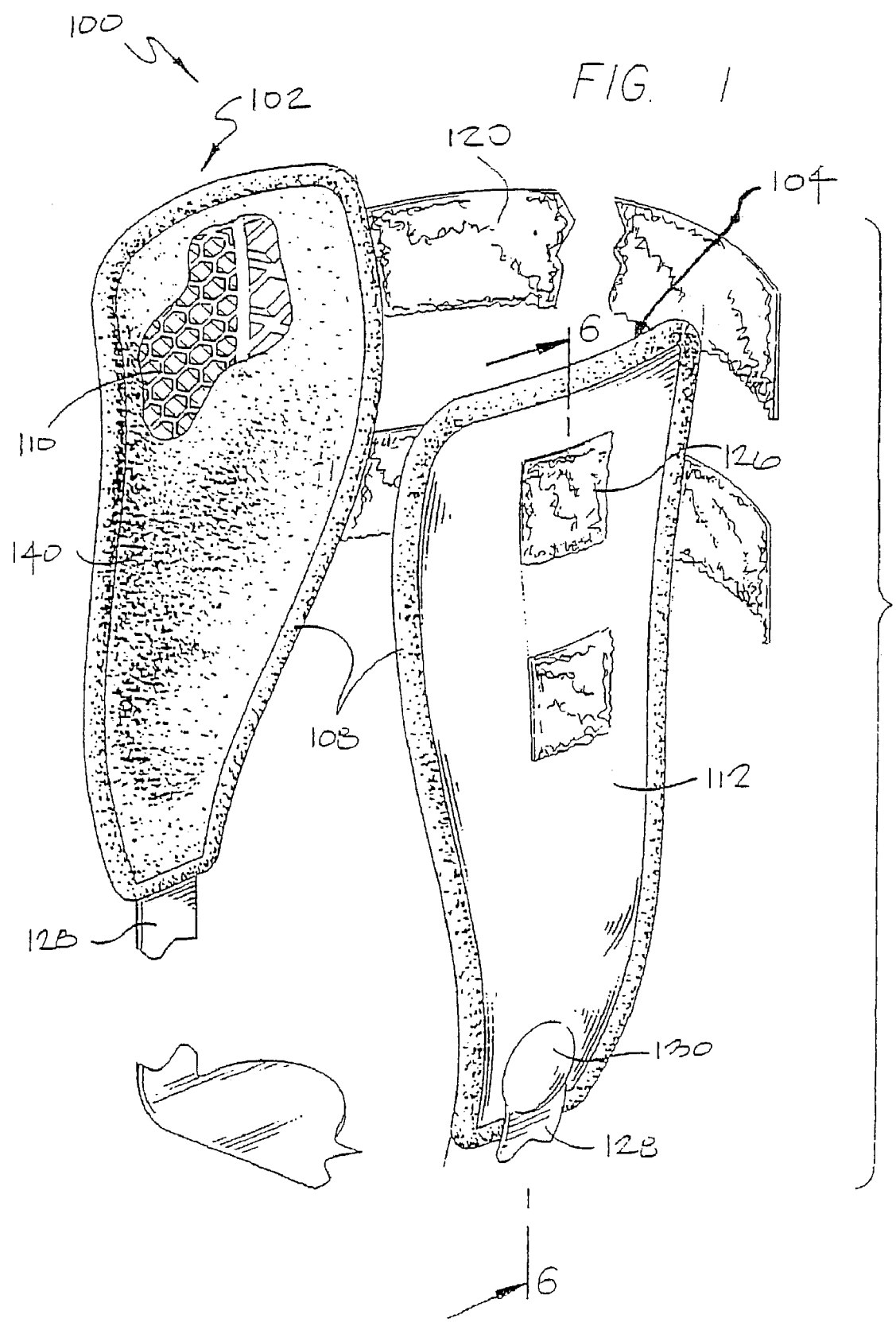
FIG. 1 is a diagrammatic, perspective view of a comfortable orthopedic support as exemplified by comfortable ankle supports illustrating the present invention.

Referring to the drawings, particularly to FIG. 1, a comfortable orthopedic support 100 is shown. As a preferred embodiment of the present invention, and to facilitate the description of the present invention, this section of the document will discuss comfortable ankle supports. However, comfortable orthopedic supports in accordance with the present invention may be manufactured for and applied to other parts of the body.

FIG. 1 illustrates an ankle brace including an ankle support 102 for the medial side of the lower leg and a cooperative ankle support 104 for the lateral side of the lower leg. However, because the ankle support design of the present invention is applicable for either one or both sides of the lower leg, the following discussions will not differentiate between the medial and the lateral side supports. The ankle support comprises a rigid outer support, or a shell, 112, and a thermoplastic elastomer (TPE) pad 110. The shell 112 and the pad 110 may be welded together or may be sealed together by an overmold 108 at least around the edges. The overmold 108 may be an extension of the TPE pad 110 and made of the same TPE material as the pad 110. A flexible layer 140 is preferably integral with pad 110, but may be separate and bonded thereto. The rigid side support 112 may be shaped to accommodate the ankle or the malleolus area. The TPE pad 110 has an inner structure as shown by the cut-away area to various geometric shapes to provide differing levels of localized comfort. The interior design of the pad 110 will be further illustrated by the following figures and the corresponding discussions below. A heel strap 128 is attached to the lower portions of both of the ankle supports by a cap 130.

The comfortable ankle support may be secured onto the lower leg using fastening fabric, such as the hook and loop type fastening material sold under the trade name VELCRO®, straps and buckles, or any other suitable means. FIG. 1 illustrates the use of the loop-type VELCRO® straps 120 along with the hook-type VELCRO® sections 126 attached to the shell 112 as the means of securing the ankle supports to the lower leg.

Although the preferred embodiment of the present invention as disclosed as being implemented using a pair of rigid side supports, the pad 110 may be used as the cushioning member for a unitary ankle support such as the "Adjustable Tension Ankle Support" disclosed by U.S. Pat. No. 4,869,267 issued to Tracy E. Grim and Thomas M. Smario.

FIG. 2 is an exploded view of an ankle support illustrating the construction of the ankle support and its internal structure. Incidentally, FIG. 2 is shown flat for convenience and clarity in showing the internal construction, but would actually be curved and contoured to the general shape of the ankle as shown in FIG. 1. FIGS. 3, 4, 8 and 12 have also been illustrated as being flat, but would actually be curved in configuration. Returning to FIG. 2, the shell 112a as illustrated may be partially covered by the TPE material 142 which may be an extension of the overmold 108a which may also cover the TPE pad 110a. The pad 110a is placed in between the outer support, or rigid shell, 112a and the inner liner 140a. The liner 140a may be of same TPE material as the pad 110a or other suitable materials such as cloth, neoprene, etc. Alternatively, the liner 140a may not be necessary if the pad 110a has a substantially continuous skin on the side of the pad upon which the liner is expected to attach to. The overmold 108a may comprise the resilient material which seals the shell 112a to the pad 110a. The inner cell structure of the TPE pad will be illustrated in detail by FIGS. 3 and 4 and described by the corresponding discussions below. If the pad 110a is welded to the shell 112a, the overmold 108a may not be a necessary element of the ankle support.

The rigid outer support, or the shell, 112a may be formed of relatively stiff or semi-rigid plastic, and may include cutouts 144 and 146 which serve to increase the shell's flexibility near the malleolus area 145 to increase the comfort and to decrease the chance of the shell 112a digging into the often sensitive ankle region. The cutouts 144, 146 may be implemented on any portion of the shell 112a to increase the flexibility of the shell 112a for the area. A receptacle 148 is provided near the bottom of the shell 112a to allow the attachment of the heel strap 128 of FIG. 1 by welding, snap-fit with a retention cap, rivet, or other suitable attaching means.

The liner 140a of the ankle support is substantially smooth. The overmold 108a as utilized substantially covers at least the outer edges of the TPE pad 110a, the liner 140a, and the shell 112a forming an air-tight seal and trapping air.

Again, if the pad 110a is welded or bonded onto the shell 112a and if the pad 110a includes a substantially continuous surface (for the side away from the shell), then the liner 140a and the overmold 108a are not necessary elements of the ankle support.

In the embodiment as shown by FIG. 2, the shell 112a surrounds but does not cover the malleolus or protruding portion of the ankle, allowing the malleolus to extend into the ankle support. That area is covered only by the outer surface of the TPE pad 110a or the liner 140a.

In an alternative embodiment, the shell itself includes the overmold about its edges. A pad is molded separately, and the edge of the pad is bonded to the overmold The liner 140a would either be molded with the lip, or would be a separate material onto which the lip 108a is molded.

FIG. 3 provides a detailed perspective view of the interior design of the TPE pad 110a. The TPE pad 110a is injection molded to include various protrusions or cells. These cells may be molded as domes, pyramidal or other regularly or irregularly shaped geometrical protrusions. The embodiment as illustrated by FIG. 3 includes various sized hexagonal cells resembling honeycomb structures 152 and 154, cylindrical cells 156, criss-cross or checkered-patterned cells 160, and irregularly shaped cells 158. The size, shape, and density of the cells as well as the thickness of the walls defining the cells determine the level of cushioning for the local areas of the ankle support.

The utilization of the injection molded TPE material for orthopedic supports has many advantages. First, the TPE pad can be molded to include detailed designs such as geometrically shaped cells. The TPE pad can be specifically contoured to the malleolus areas, the calf, and the calcaneal regions of the support. Although the TPE material is more dense than other padding materials such as foam, the innovative design including molded cell-structure as illustrated by FIGS. 2-7 overcomes this disadvantage by reducing the weight of the product. The reduction in the weight of the pad also translates into lower cost and increased value to the end user of the product.

One suitable thermoplastic elastomer (TPE), is available under the name RIMFLEX, made from KRATON® Polymer. It is produced by Shell Oil Company and is available from Synthetic Rubber Technologies of Uniontown, Ohio. There are many other sources of thermoplastic elastomers. The material may be molded by any of the numerous injection-molding companies across the nation. Other material may be used in place of the TPE, including thermosetting and thermoplastic materials.

Continuing to refer to FIG. 3 but also referring to FIG. 4, the geometrically shaped cells of the pad 110 may be interconnected via channels 162 and 164 as illustrated by FIG. 4. The figure illustrates channels 162, molded between the cells of the TPE pad 110a to allow passage of air or fluids amount the cells of the pad 110a. The channels provide the means for the movement of the air or fluids between the cells, creating a massaging effect on the lower leg, thereby promoting blood flow. Also, the channels may be designed in a manner in which external fluid may be circulated with the ankle pad for hot and cold therapies.

FIG. 4 also illustrates the fact that the cells of the pad 110a may be molded to include shapes such as logos and trademarks as well as geometrical shapes as indicated by reference number 165.

FIG. 5 is a partial transverse cross-sectional view of the TPE pad embodiment as shown in FIG. 4 taken along the line 5-5. The geometric cells 111 are defined by its walls 113. In the embodiment as shown, the pad 110a includes a smooth, substantially continuous side 110b eliminating the need for a liner 140 of FIG. 2 for this embodiment. However, even though not required, a liner 140b still may be used to increase comfort.

FIGS. 4 and 5 also illustrate that the cells of the pad 110a may include openings 163 on its smooth side allowing air to pass in and out of the pad to relieve pressure. If the liner 140b is made of cloth or other breathable material, the openings 163 do not have to extend through the liner 140b.

Referring now to FIGS. 6 and 7, cross-sectional side views illustrating the internal structure of the ankle supports of FIG. 1 are illustrated. Referring specifically to FIG. 6, a cross-sectional side view of the ankle support is illustrated. The shell 112 provides rigid or semi-rigid support for the ankle support and the TPE pad 110 provides the cushioning for the ankle support. The TPE pad 110 includes geometrically shaped cell structures. The overmold 108 may seal the TPE pad 110 and the liner 140 to the shell 112. If the seal is an air-tight seal, and the liner 140 (which is an integral part of the pad 110) includes no openings as illustrated by the reference number 163 of FIG. 4, then a bladder is formed. In the embodiment as shown, the shell 112 covers the entire lower leg including the malleolar area. Also, the TPE pad 110 may include a smaller, internal bladder 172 around the malleolus area providing additional level of cushioning.

Alternatively, instead of a bladder 172, the additional cushioning may be provided by inserting other soft material in the space such as open cell foam material or gels.

Reference number 117 shows that the structures for the pad 110 may be formed such that the TPE material does not span the entire distance from the liner 140 to the shell 112 creating a pressure free travel of the padding 110 to the shell 112. The pressure free travel design provides for unsurpassed softness and comfort for the area of the pad. This technique allows additional air to be trapped under the pad 110 and creates additional room for the pad 110 to flex for softer cushioning. Also, the reduction in the amount of material used for the pad 110 leads to a lighter ankle support and reduced production costs.

An alternative embodiment of the ankle support is illustrated by FIG. 7. Similar to the ankle support as shown by FIG. 6, the shell 112c and the TPE pad 110c are sealed to each other by an overmold 108c substantially molding at least the edges of the shell 112c and the pad 110c. However, unlike the embodiment of FIG. 6, the pad 110c of FIG. 7 does not include internal geometric structures for cushioning. The pad 110c includes only an internal bladder 172c around the malleolus area.

In the embodiment of the present invention as illustrated by FIG. 7, the cushioning is provided by internal structures molded directly onto the shell 112c as illustrated by reference number 119. In this embodiment, the cell structures for the padding, such as the geometric configurations shown in other figures, has been initially molded directly on the shell 112c. Subsequently, the layer 108c is bonded to the shell 112c around the edges of the shell, leaving the open spaces defined by the molded cell structures 119.

Utilizing the geometrically shaped cells molded onto the TPE pad, the ankle supports 102, 104 of FIG. 1 may provide differing levels of cushioning to the different areas of the lower leg being protected by the ankle support. FIG. 8 illustrates one possible map of the areas of the ankle support which may require different levels of cushioning. For instance, the malleolus area 188 may require very soft support using a configuration indicated by reference number 117 of FIG. 6 or could be provided by an internal bladder-type structure 172c as shown in FIG. 7. Using the construction shown at 117 in FIG. 6 would allow some distance for free travel, with increasing resistance, and protection against bottoming out. The area 186 surrounding the malleolus may require a soft cushioning, slightly firmer than the area 188, to avoid aggravation of an injured malleolus. The area 184 supporting the lower tibia may require firm support and its surrounding area 182 may require softer cushioning for comfort. The softer cushioning around the edges of the support prevents the edges of the shell from digging into the wearer's leg. As already indicated, the degree of cushioning of these areas may be predetermined. Other mapping schemes may be used to support the ankle region or to support other limbs of the body.

An alternative embodiment of the orthopedic support 200 is illustrated by FIG. 9. The ankle supports 202 and 204 of this embodiment of the orthopedic support 200 include other cushioning materials in addition to TPE pads as described above. The additional cushioning may be provided by the embedded cushioning material 212. Typically, the material used for the embedded cushioning is foam or gels. Because the TPE material is more durable (tear-resistant), flexible, water resistant, and hypoallergenic than foam material, it makes a better padding for ankle supports. However, because of its higher density, it may not provide cushioning which is as soft as may be desired, and could involve some increase in weight. Using the design illustrated by FIG. 9, the benefits of the TPE pad may be retained while gaining the additional cushioning and reduction in weight, provided by the foam core 212.

In short, FIGS. 1-8 illustrate an embodiment of the ankle support of the present invention where the padding for the support is created using injection molded TPE pads with internal geometrically shaped cells. Alternatively, FIGS. 9-11 illustrate an embodiment of the ankle support of the present invention where the padding for the support is created using a molded TPE pad with a cushioning core of a different material.

Also illustrated by FIG. 9 is the adjustable heel strap 228 which may be detachably mounted to the ankle supports using the loop and hook type mounting member 236 which, in turn can be affixed to the lower portion of the ankle supports permanently or by a snap-on unit or other suitable attaching means.

The shell 112d of the ankle support 202, 204 may be formed to surround but not cover the malleolus area 114d, with the trampoline cushioning effect resulting from the lack of rigid coverage in the malleolus area allowing less padding in that area.

Referring to FIGS. 10 and 11, cross-sectional side views illustrating the ankle support pad structure, taken along lines 10-10 of FIG. 9 is shown. The foam pad 212 is embedded in the TPE pad 110d between the shell 112d and the outer surface 140d of the TPE pad 110d. This construction increases the cushioning of the TPE pad 110d while maintaining the water resistance, durability, and other favorable characteristics of the TPE pad.

Alternatively, for the cross section of the ankle support as illustrated by FIG. 11, the embedded foam pad 212a, 212b does not cover the malleolus area. Rather, the foam pad surrounds the malleolus area as indicated by 212a and 212b. As illustrated by FIG. 11, only a layer of the TPE pad 110d covers the malleolus area. This creates a "trampoline" type effect. The malleolus, as illustrated by the figure, is covered by a TPE "trampoline," which provides a flexible padding without the rigid shell. The foam pad 212a and 212b of may be replaced by gel because, unlike the design illustrated by FIG. 10, the space defined 212a and 212b is completely enclosed by the TPE over pad 110d.

FIG. 12 illustrates an adjustable shell design applicable to the present type of ankle support. The shell 112e may comprise a rigid or semi-rigid plastic shell frame 220 and a shell core 222 which may be removable. The removable shell core 222 may be replaced with more or less rigid shell cores as the needs of the patient change over time. The initial shell core 222 may be of a very rigid material so that prevention of inversion or eversion is greatest, thereby allowing the patient to regain stability in his or her ankle. Once the ankle has healed and the patient is ready for more demanding forms of exercise, the shell core 222 may be changed to a less rigid material so as to allow further movements of the ankle. Further, the shell core 222 may be removed entirely for further flexion, if desired. In the embodiment as illustrated by FIG. 12, the shell core 222 fits snugly into the shell frame 220, and snaps into place. The snapping action is accomplished using a protrusion 224 and the indentation 226.

The arrangement of FIG. 12 can also be employed as a "trainer" style ankle support to prevent injury to an ankle that has healed somewhat but which requires protection from re-injury. In the "trainer" embodiment, the outer shell 220 is made from a flexible material such as a low-density polyethylene or polypropylene. An insert 222 may be made from a material that is more rigid than the flexible outer shell 220, such as high-density polyethylene, steel, nylon, and other rigid materials.

In the preferred embodiment that FIG. 12 illustrates, the insert 222 snaps into place on the shell 220. However, the insert may alternatively be secured to the shell 220 in other ways, such by riveting, with adhesive, or by welding into place. An advantage of this arrangement is that the insert 222 may be secured into place immediately after the ankle is injured. However, after the ankle has healed somewhat, the insert 222 may be removed from the outer shell 220, making the support more flexible and allowing the person wearing the support to engage in a wider variety of activities.

Figure 13:
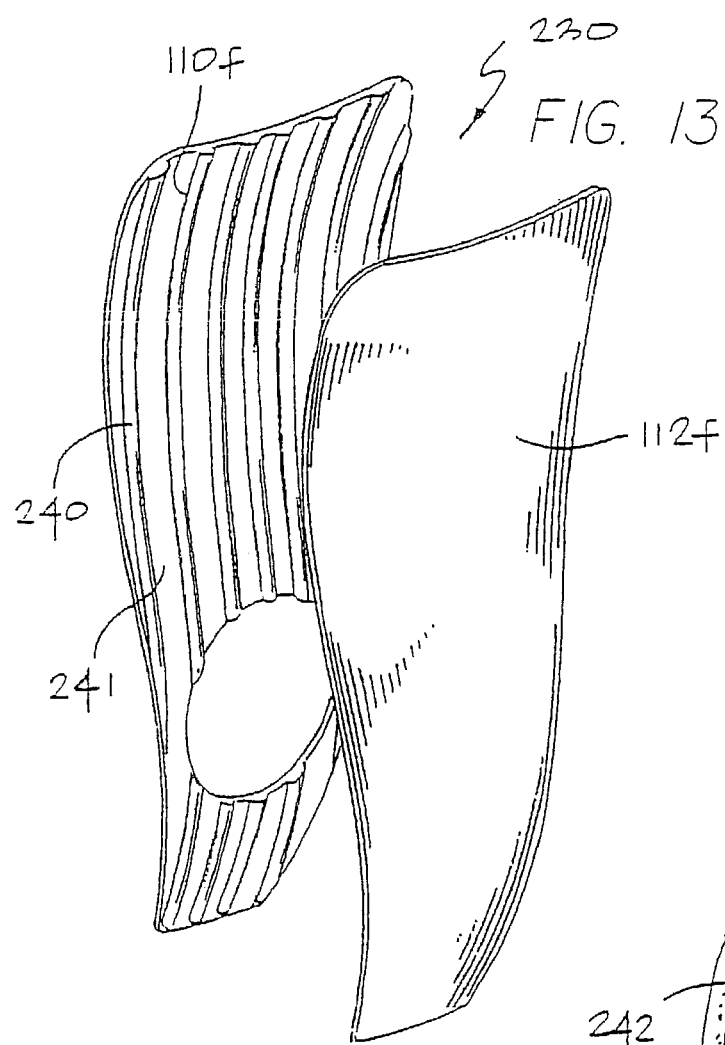
FIG. 13 illustrates an alternative embodiment of the ankle support and pad in which a channeled pad is employed.
Figure 14:
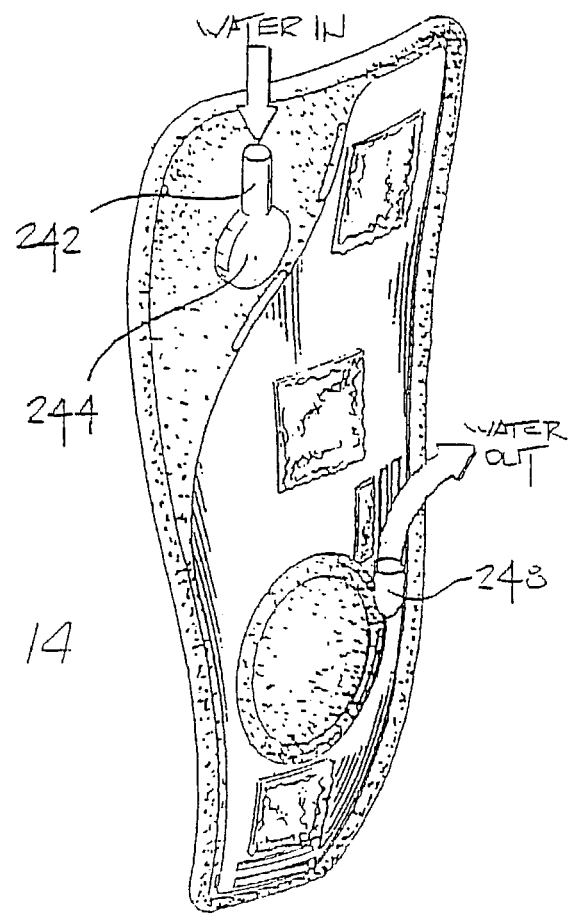
FIG. 14 illustrates inlet and outlet ports and valves of an ankle support useful for hot and/or cold therapy.

Yet another alternative embodiment of the ankle support is illustrated by FIGS. 13 and 14. Referring to FIG. 13, the ankle support 230 is illustrated with a shell 112f and the TPE pad 110f with molded tubular channels 240 and grooves 241 as its inner surface. Such design is particularly useful for hot and cold treatments of the ankle and the lower leg. FIG. 14 illustrates a water intake port 242 and an intake valve 244 and a water outlet port and an outlet valve 248.

Figure 15:
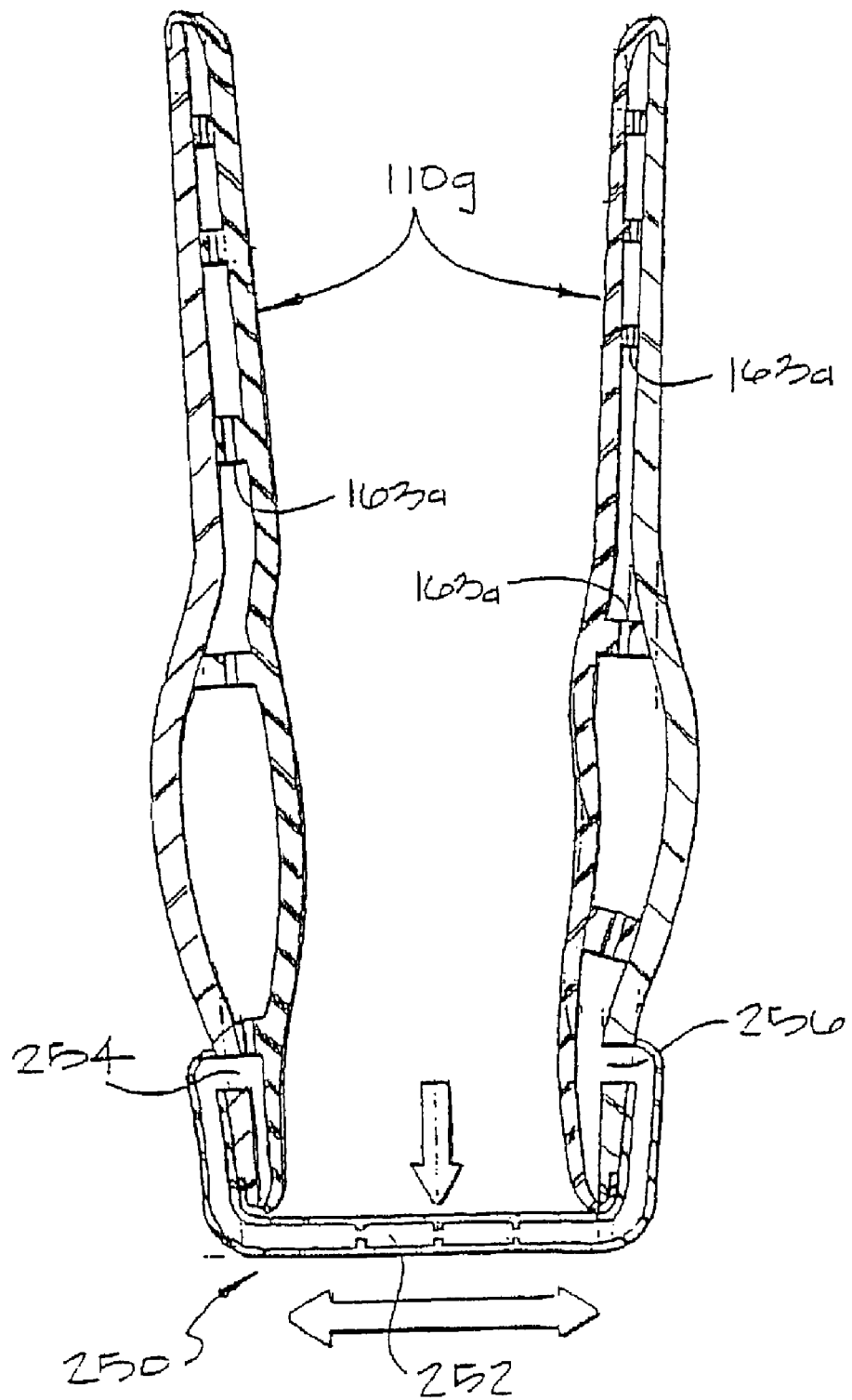
FIG. 15 is a cross-sectional view of another embodiment of the present invention.
Figure 16:
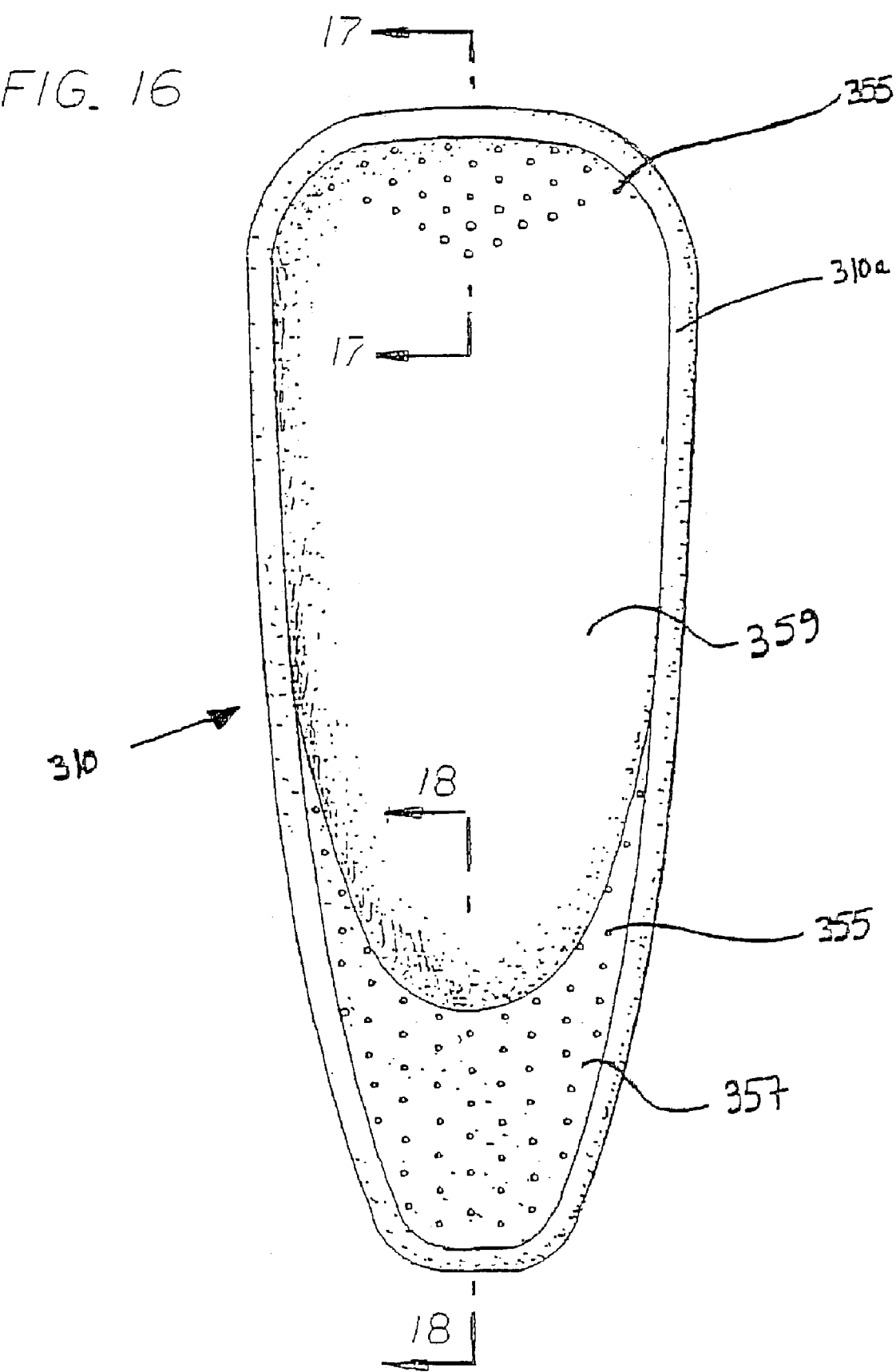
FIG. 16 is a rear elevational view of the exterior of an alternative embodiment of a pad according to the present invention.

Another alternative embodiment of the orthopedic support of the present invention is illustrated by FIG. 15. The heel member 250 comprises a bladder 252 linked via channels 254, 256 to the ankle supports which has its TPE pads 110g configured as bladders as well. Each time the foot of the wearer presses down on the heel member 250, the air or the fluid within the bladder 252 is pressured into the bladder-pad 110g of the ankle supports thereby massaging the lower leg. The pads or bladders 110g may be as shown in earlier figures of the drawing, and may have channels 163a interconnecting the cells of the pads. The channels 254, 256 may be formed integrally with the heel bladder 252, or separate air channels or tubes may be provided to interconnect the heel bladder 252 with the side pads 110g.

FIGS. 16-20 illustrate a further alternative embodiment of the present invention. In this embodiment, the support is provided with a plurality of thin "fingers" 321, which are most clearly seen in FIGS. 17 and 18. The fingers 321 are molded about the periphery of the respective honeycomb cells 352 and 353. The fingers extend from the molded interior elastomer pad 310 of the support to the hard outer plastic shell 312 (FIG. 20). The entire interior elastomer pad 310, which has an edge 310a, can be molded in a single injection-molding step to simplify manufacturing.

The aspect ratio of the fingers 321 are varied to provide more or less cushioning in particular regions of the support. For example, FIG. 18 illustrates the change in finger heights in different regions of the pad, including longer fingers 321a and shorter fingers 321b. In much of the support, the fingers 321b are relatively short with respect to the diameter of the fingers. On the other hand, the fingers 321a are considerably longer than the fingers 321b in the rest of the pad. Consequently, the area or areas of the support having the longer fingers 321a will provide more cushioning than the areas of the support having the shorter fingers 321b. That is, the longer fingers 321a flex more than the shorter fingers 321b in response to pressure on the support from the ankle.

The fingers 321(a)(b) also serve to space the flexible inner portion of the support from the hard outer portion of the support. Consequently, the longer fingers 321a provide additional space between the malleous of the ankle and the hard outer shell 312 of the brace. The malleolar region of the ankle is typically where the ankle is injured, and the injury may be exacerbated if the injured portion of the ankle hits the hard outer shell of the support. The longer fingers prevent the malleous from hitting the hard outer shell during use, and provide softer cushioning which makes the brace more comfortable for the wearer during healing.

It should be noted that the outer shell 312 in FIG. 20 includes air holes 315a that allow air within the support to ventilate in and out. In this embodiment of the invention, the cells support the ankle without the need for pressurized air. That is, the structure of the cells themselves rather than pressurized air provide the support for the ankle. This is in contrast to pressurized-air types of supports, which do not provide cushioning unless the support is inflated prior to use.

Additional air holes 355 may be included in the pad 310 itself. For example, the pad 310 in FIG. 16 has numerous air holes in both the bottom and top portions of the pad. Consequently, air is free to flow in and out of the spaces between the pad and the shell. This may be advantageous in, for example, high altitude locations where the air pressure in an air-filled bladder relative to the ambient pressure may become greater than desirable. The present embodiment of the pad, which does not inflate with air, therefore does not have a problem with air pressure in high altitudes.

As an additional alternative, the thickness of the pad walls may vary in different regions of the pad. For example, the wall thickness of the pad of FIG. 18 is greater in the lower region of the pad 357 than in rest of the pad 359. This is because the lower region of the pad generally corresponds to the area of the ankle that is injured and where there is swelling. Increasing the thickness of the skin causes the pad to feel firmer, and decreasing the thickness makes the pad feel softer.

A pad having varying skin thickness is preferably formed by injection molding. However, other methods in which a liquid material solidifies to form to the shape of the mold, such as (for example) reaction-injection molding or pour molding may be employed. To vary the thickness of the skin of the pad while at the same time forming a pad cell structure and integral fingers generally requires a manufacturing method in which a liquid material fills a cavity defining the desired pad configuration, then solidifying to conform the shape of the pad to the shape of the cavity.

Referring in particular to FIGS. 20 and 21, the shell 312 is provided with an overmold 308 that extends about the periphery of the shell. The overmold is typically formed of the same material as the pad 310, so that the pad can be easily bonded to the overmold. The overmold 308 has a ridge 309 about which the outer edge 310a of the pad extends when the pad is bonded to the overmold. The fingers 321 extend from the pad 310 to the shell 312, with the outer surface of the pad 310 being substantially continuous.

In the presently preferred embodiment, the pad 310 bonds only to the overmold 308 to secure the pad to the shell. The pad is typically bonded to the overmold with a conventional solvent that melts material on both the edge 310a of the pad and on the overmold. The melted material then solidifies to form the bond. However, the pad may be bonded to the overmold in other ways, such as by welding or with adhesives. In alternative embodiments, the pad may be adhered directly to the shell.

In the preferred embodiment of the present invention as illustrated by FIGS. 1-15, a comfortable orthopedic support is implemented with ankle supports and a heel strap. The ankle supports comprise a rigid shell and padding made from molded thermoplastic elastomer (TPE) with or without other padding material. The TPE pad may be sealed to the shell with trapped air or fluid between the pad and the shell to form a bladder. A lining material may cover the pad. To provide localized comfort, the TPE pad may be molded to include various protrusions or cells toward the shell. These cells may be shaped as domes or other geometric shapes such as honeycomb shapes. Alternatively, soft foam may be embedded between the rigid shell and the durable TPE padding to provide durable surface with soft padding. Another option is to use gel in place of the soft foam or the molded TPE pad. Typically, the overmold which seals the TPE pad to the shell is made of same TPE material as the padding and also partially covers the shell.

Although the present invention has been described in detail with regarding the exemplary embodiments and drawings thereof and with regarding alternate embodiments, it should be apparent to those skilled in the art that various adaptations and modifications of the present invention may be accomplished without departing from the spirit and the scope of the invention. Thus, by way of example and not of limitation, the present invention has been described as an ankle support. However, it is apparent that the inventive support may be applied to arms, legs, and other part of the body requiring varying degrees of localized comfort. Incidentally, where reference is made hereto to air cells or geometric cells, reference is to macro-cells with dimensions greater than 1/64 or 1/32 of an inch for example, and not to foams. Accordingly, the invention is not limited to the precise embodiment shown in the drawings and described in detail hereinabove.

Pads according to some of the embodiments of the present invention may be sealed, such that a space is formed between the pad and the shell that can be filled with air or other fluid to form a fluid bladder. The shell may include an air pump with which the user can inflate the bladder. A release valve can be provided permitting the user to release air from the bladder as necessary.

It should be noted that the cell structure described in connection with the present invention has additional applications. For example, open cells can be inserted in between two layers of material which together form a bladder. The cells act as reinforcement to the bladder, such that if the bladder deflates or if an especially great load is applied to the bladder, the cell structure reduce the likelihood that the bladder will bottom out.

While a pad made with a TPE material has been described, and while the inventors presently prefer to make the pad from TPE material, it should be understood that the pad may be made from a variety of other materials. For example (but without limitation) the pad may be made of thermoplastic urethanes, thermoplastic rubbers, silicones, two-part urethane mixtures and poured foams.

It should be noted that the fingers 321 are shown in the figures as having a generally circular cross-section. However, the fingers can have various other cross-sections, so long as they perform a cushioning function.

While the pads described herein are particularly well suited for use in orthopedic supports, there are numerous other applications in which such pads could be employed. For example, embodiments of this type of pad may be employed in various protective devices, such as kneepads, shin guards, and football pads, among other applications where durability and water resistance is desired.

Considering now a further alternative embodiment illustrated in FIGS. 22-26, a shell 990 having an overmold 992 is provided. There are two separate shell pieces used in a complete ankle brace, although only one shell piece is illustrated. The shell pieces are interconnected with a hinged heelpiece, as described previously.

An outer pad 1000 with cells 1002 provides support and helps to protect the bladder from puncture by foreign objects. The pad 1000 also provides additional cushioning to help ensure that the bone or the skin is protected from contacting the shells during impact. In the embodiment illustrated, the cells 1002 are generally contained within an ovular area 1004 in the bottom portion of the pad corresponding to the malleolus of the ankle. In the illustrated embodiment, the cells are ovular in shape, although other shapes may be employed.

Figure 23:
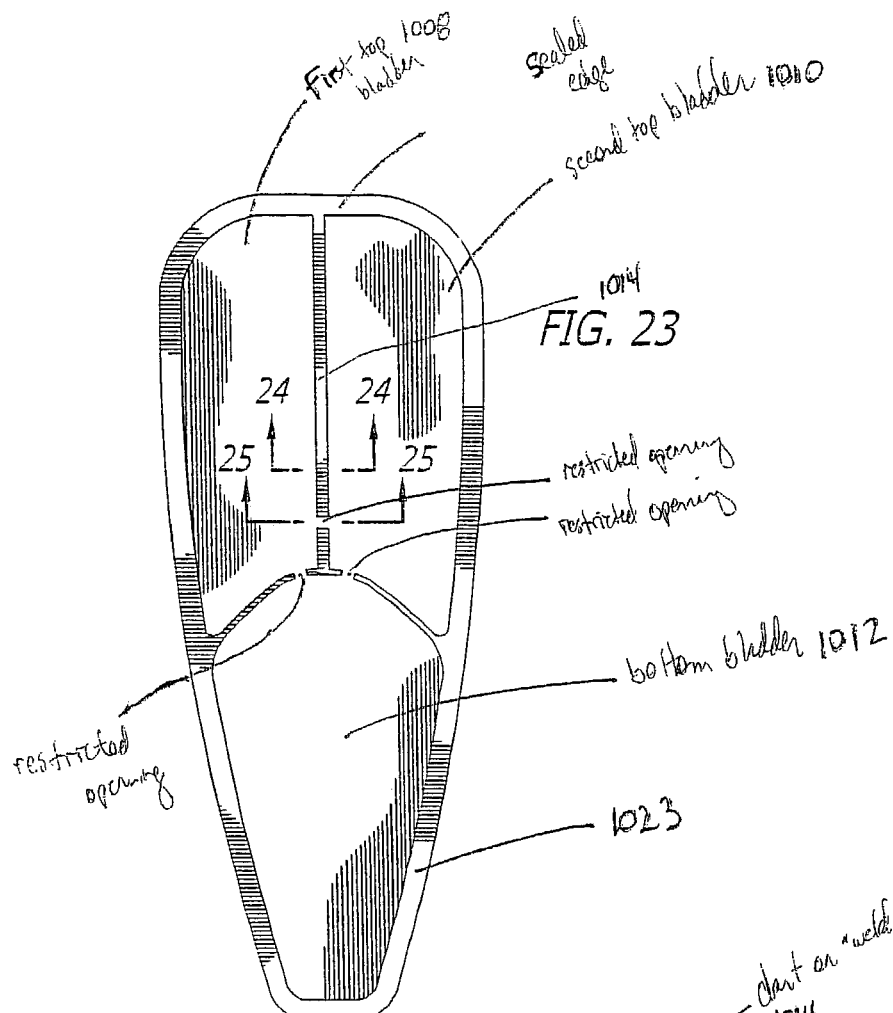
FIG. 23 is a front view of a bladder pad.
Figure 24:
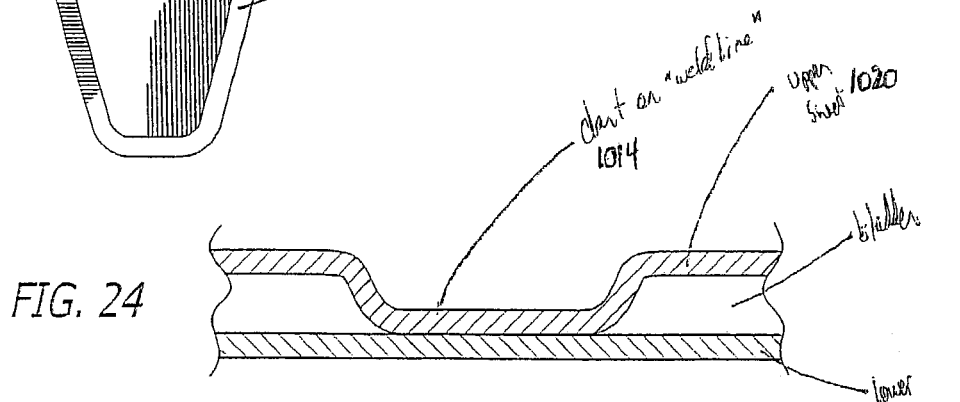
FIG. 24 is a cross-sectional view showing a weld line.

In FIGS. 23 and 24, the embodiment illustrated shows a bladder pad 1006 having three bladders 1008, 1010, and 1012 formed on the bladder pad. The bladders are separated by weld lines 1014, 1016, and 1018, which are further illustrated in FIG. 24. The bladder pad is formed from a top layer 1020 and a bottom layer 1022, which are welded together. The bladder pad edge 1023 seals the bladder pad.

Figure 25:
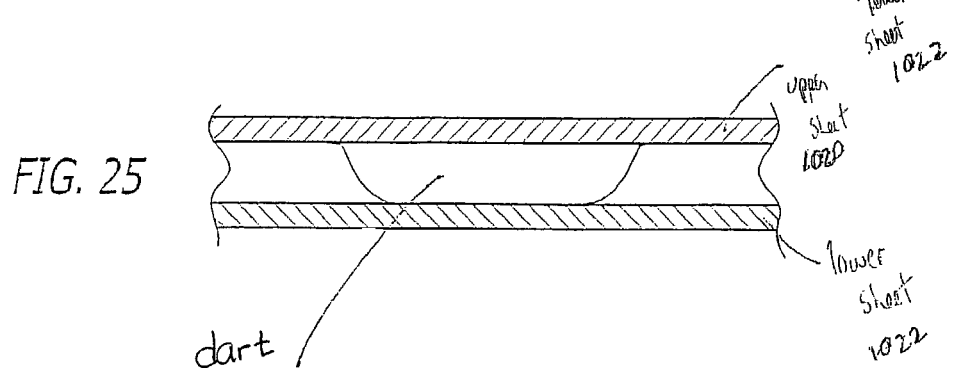
FIG. 25 is a cross-sectional view showing a restricted airflow passage.

Alternative embodiments may have more or fewer bladders. The preferred embodiment of the air bladder has restricted openings 1024 and 1026 from the bottom bladder to the top two bladders. As pressure is applied to the bottom bladder, the air transfers to the top two, but it transfers at a slower rate than if the openings were not restricted. The rate of air transfer can be adjusted by opening or narrowing that gap, or lengthening or shortening it. FIG. 25 is shows a cross section through the opening 1028 which is a created by breaking the weld line 1014. This break is created by not welding the films together in that area.

The restricted openings 1024, 1026 and 1028, and the resulting controlled movement of air provide a unique "feel" to the ankle brace. The transfer of air through the restricted openings provides a more fluid, somewhat gel-like feel when pressure from the ankle is applied. Generally, the restricted openings slow the air transfer process, as compared to a bladder having no airflow restrictions. The air transfer reduces the likelihood that the pad will bottom out upon pushing down on it. Once the pressure is taken off the bladder, the air pressure equalizes itself among the bladders that are connected to one another.

In the preferred embodiment, the bladder is filled only with air, and is not filled with foam, for example. However, in alternative embodiments, the bladder may be filled with gases other than or in addition to air, and/or may include foam or other filler material. In particular embodiments, a restricted opening 1028 between the top two bladders may be formed, although this is not required.

The bladder pad 1006 may be made of welded sheets of vinyl film, or urethane, or any other film that will hold air. The welding is typically RF welding, although other types of welding known in the art may be used. One method of welding is discussed in U.S. Pat. No. 5,026,389, which is incorporated by reference herein. The bladder pad 1006 may be attached to the shell by way of adhesive, such as double sided tape or spray adhesive.

In the embodiment illustrated, the top portion of the bladder pad has two smaller bladders separated by a "dart," or weld line. With two smaller bladders as opposed to a single large bladder, the bladder is less likely to bottom out. The dart serves to limit the expansion of each smaller bladder, there by reducing the overall thickness of the bladder when pressurized. Specific darting patterns can be utilized to create different shapes and thickness pads, depending on the requirements of the specific application.

Concerning the size of the openings, the size of the opening determines the amount of air and the speed in which the air is transferred from one area of the bladder to another. In one embodiment, the restricted openings are 0.125" wide. The top two bladders have a width of approximately 1.5" each. The bottom bladder, at its widest point, measures 2.5" wide, and 1.0" at the narrowest, in one embodiment.

As described previously, the cell pad has cell walls that collapse under pressure. This effectively works to provide additional cushioning for the brace. FIG. 26 shows a tapering of the height of the resilient walls 1003 of the cells 1002 toward the edges of the ovular area 1004. At the distal end of the pad, for instance, it is desired to reduce the thickness of the pad, so that the pad will fit into a shoe more comfortably. The cushioning is also not needed nearly as much at the bottom of the pad, so this reduction in height does not reduce the overall comfort of the brace. The cells walls 2003 may also taper off in height toward the edges of the oval. Once again, this is done to reduce the overall thickness of the brace where it goes into a shoe and additional padding is not as needed.

Considering now the embodiment of FIG. 27, a velcro loop layer attached to a bladder pad 1008 attaches the bladder pad to the shell 990. A velcro hook 1040 is attached to the shell 990 to receive the velcro loop layer on the bladder pad. A cell pad 1002 overlays the bladder pad 1008.

In addition to the embodiment shown in FIG. 27, the current invention may employ the bladder arrangement of FIG. 27, without the cell pad 1000. In such an arrangement, the Velcro loop layer 1042 would include a foam layer for additional padding and protection from the shell between the Velcro layer 1042 and the bladder pad 1008. This foam layer could be located on the shell side of the bladder pad 1008, or on the skin side of the bladder pad 1008.

These alternative embodiments may make use of the overmold and pivoting heel strap, as desired. The bladder concept is not limited to ankle braces, but may be extended to other types of orthopedic supports, such as wrist braces and knee supports. Wrist braces and knee supports are known in the art. A multiple bladder pad may be added to the layers of material in existing wrist braces or knee supports, or may be added in place of an existing layer in a prior art structure.

From the foregoing detailed description, it will be evident that there are a number of changes, adaptations, and modifications of the present invention which come within the province of those skilled in the art. However, it is intended that all such variations not departing from the spirit of the invention be considered as within the scope thereof as limited solely by the claims appended hereto. It is therefore intended that the following claims may be interpreted as covering all such applications, alterations and modifications as fall within the true spirit and scope of the invention.

We claim:

1. An ankle brace comprising: at least one semi-rigid shell member for extending aver the ankle and the lower leg on side of the ankle, a sealed bladder pad mounted to said shell member on the side of said shell member facing the ankle; said bladder pad including three small interconnected bladders on the pad, wherein a first larger bladder is mounted at the lower end of said shell, and two side-by-side upper bladders are mounted on an upper portion of the associated shell member, and said three bladders having openings permitting limited flow of air between said bladders; whereby when a patient wearing said ankle braze walks, the lower bladder is compressed, and air is directed through said openings to said upper bladders, thereby intermittently varying the pressure on the ankle and lower leg, and promoting circulation.

2. An ankle brace comprising: at least one semi-rigid shell member for extending over the ankle and the lower leg on a side of the ankle, a sealed bladder pad mounted to each of said shell members on the side of said shell member facing the ankle; said bladder pad including three small interconnected bladders wherein a first larger bladder is mounted at the lower end of said shell, and two side-by-side upper bladders are mounted on an upper portion of the associated shell member, said three bladders having openings permitting limited flow of air between said bladders; and resilient cushioning material mounted to each said shell on the side of said shell facing the ankle; whereby when a patient wearing said snide brace walks, the lower bladder is compressed, and air is directed through said restricted openings to said upper bladders, thereby intermittently varying the pressure on the ankle and lower leg, and promoting circulation.

3. An ankle brace as defined in claim 2 wherein said cushioning material is a thin layer of resilient material substantially coextensive with each said bladder.

4. An ankle brace as defined in claim 2 wherein said cushioning material is a resilient plastic sheet with geometric shapes thereon extending outward from said plastic sheet toward said shell.

5. An ankle brace as defined in claim 3 wherein bonded to said bladder pad is a loop type laminate padding material, and wherein hook type material is bonded to said shells for hook and loop type mounting of said bladder pad to said shells.

6. An ankle brace comprising: at least one semi-rigid shell member for extending over the ankle and the lower leg on one side of the ankle, a sealed bladder pad mounted to said shell member on the side of said shell member facing the ankle; said bladder pad including a plurality of interconnected bladders wherein said interconnecting bladders are entirely sealed with the periphery of said bladder pad; at least two of said bladders having openings permitting limited flow of air between said at least two bladders; and a resilient pad having a matrix of cells having walls forming resilient geometric shapes thereon extending toward said shell.

7. An ankle brace of claim 6, wherein the resilient geometric shapes are in the lower half of said resilient pad.

8. An ankle braze of claim 6, wherein said geometric shapes are ellipses.

9. An ankle brace of claim 6, wherein an overmold substantially surrounds said pad and said shell substantially sealing together said orthopedic support.

10. An ankle brace as defined in claim 6, further comprising an overmold molded onto said shell, said pad being bonded to said overmold.

11. An ankle brace as defined in claim 6, further comprising means for securing said ankle support around the lower leg.

12. An ankle brace as defined in claim 6, wherein said pad further comprises a plurality of integrally molded fingers extending from said pad to said outer shell.

13. An ankle brace as defined in claim 12, wherein said fingers are integrally molded with said pad.

14. An ankle brace as defined in claim 12, wherein some of said fingers have a different length than others of said fingers.

15. An ankle brace as defined in claim 6, wherein said pad is formed of a thermoplastic elastomer (TPE).

16. An ankle brace as defined in claim 6, wherein said brace further comprises a layer of cushioning in between said bladder pad and said semi-rigid shell member.

17. An ankle brace as defined in claim 6, wherein said brace further comprises a layer of cushioning in between said bladder pad and said resilient pad.

* * * * *